United States Patent
Shiroya et al.

(10) Patent No.: US 11,452,676 B2
(45) Date of Patent: Sep. 27, 2022

(54) COMBINATION OF POLYION COMPLEX PARTICLE AND NON-POLYMERIC BASE HAVING TWO OR MORE DISSOCIATION CONSTANTS

(71) Applicant: L'Oreal, Paris (FR)

(72) Inventors: Toshifumi Shiroya, Kawasaki (JP); Hidehiko Asanuma, Kawasaki (JP); Takehiko Kasai, Kawasaki (JP)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/618,755

(22) PCT Filed: Jun. 8, 2018

(86) PCT No.: PCT/JP2018/023046
§ 371 (c)(1),
(2) Date: Dec. 2, 2019

(87) PCT Pub. No.: WO2018/230739
PCT Pub. Date: Dec. 20, 2018

(65) Prior Publication Data
US 2020/0155426 A1    May 21, 2020

(30) Foreign Application Priority Data

Jun. 13, 2017 (JP) .............................. JP2017-115766

(51) Int. Cl.
| | | |
|---|---|---|
| *A61K 8/02* | (2006.01) | |
| *A61K 8/44* | (2006.01) | |
| *A61K 8/64* | (2006.01) | |
| *A61K 8/73* | (2006.01) | |
| *A61K 8/81* | (2006.01) | |
| *A61K 8/88* | (2006.01) | |
| *A61Q 19/00* | (2006.01) | |

(52) U.S. Cl.
CPC .............. *A61K 8/0241* (2013.01); *A61K 8/44* (2013.01); *A61K 8/64* (2013.01); *A61K 8/731* (2013.01); *A61K 8/733* (2013.01); *A61K 8/735* (2013.01); *A61K 8/8117* (2013.01); *A61K 8/8147* (2013.01); *A61K 8/88* (2013.01); *A61Q 19/00* (2013.01)

(58) Field of Classification Search
CPC .............. A61K 8/0241; A61K 2800/54; A61K 2800/542; A61K 8/0216; A61K 8/44; A61K 8/64; A61K 8/731; A61K 8/733; A61K 8/735; A61K 8/736; A61K 8/8117; A61K 8/8147; A61K 8/88; A61Q 19/00
See application file for complete search history.

(56) References Cited

U.S. PATENT DOCUMENTS

| | | | | |
|---|---|---|---|---|
| 2007/0077292 A1* | 4/2007 | Pinsky | ................. | A61K 31/728 424/450 |
| 2008/0317795 A1* | 12/2008 | Traynor | ................. | A61Q 19/10 424/401 |

FOREIGN PATENT DOCUMENTS

| | | | | |
|---|---|---|---|---|
| JP | 2005-036190 A | 2/2005 | | |
| JP | 2008-280407 A | 11/2008 | | |
| JP | 2014-227389 A | 12/2014 | | |
| JP | 2015-107939 A | 6/2015 | | |
| KR | WO 2008/126971 A1 * | 10/2008 | ............... | A61K 8/19 |
| WO | WO 2010/127154 * | 11/2010 | ............... | A61K 9/16 |
| WO | 2013/153678 A1 | 10/2013 | | |

OTHER PUBLICATIONS

Inusa et al.; European Polymer Journal, 81:198-215; 2016.*
Akagi, T., et al., "Stabilization of polyion Complex Nanoparticles Composed of Poly(amino acid) Using Hydrophobic Interactions," Langmuir 26(4):2406-2413, 2010.
Hsieh, Y.-H., et al., "Shell and Core Cross-Linked poly(L-lysine)/poly (acrylic acid) Cmplex Micelles," Soft Matter 10(47):9568-9576, 2014.
Insua, I., et al., "Polyion Complex (PIC) Particles: Preparation and Biomedical Applications," European Polymer Journal 81:198-215, 2016.
International Search Report dated Oct. 18, 2018, issued in corresponding International Application No. PCT/JP2018/023046, filed Jun. 8, 2018, 3 pages.
Park, S.Y., "Biopolymer Composite Films Based on κ-Carrageenan and Chitosan," Materials Research Bulletin 36:511-519, 2001.

* cited by examiner

*Primary Examiner* — Jeffrey T. Palenik
(74) *Attorney, Agent, or Firm* — Christensen O'Connor Johnson Kindness PLLC

(57) ABSTRACT

The present invention relates to a composition, preferably a cosmetic composition, and more preferably a skin cosmetic composition, comprising: (a) at least one particle, comprising at least one cationic polymer, at least one anionic polymer and at least one non-polymeric base having two or more pKb values or salt(s) thereof; and (b) at least one physiologically acceptable volatile medium. The composition according to the present invention is stable, and can have a variety of cosmetic functions.

14 Claims, No Drawings

US 11,452,676 B2

COMBINATION OF POLYION COMPLEX PARTICLE AND NON-POLYMERIC BASE HAVING TWO OR MORE DISSOCIATION CONSTANTS

TECHNICAL FIELD

The present invention relates to a composition including polyion complex particles and a film of polyion complex particles, as well as a process for preparing a film by using polyion complex particles and a use of polyion complex particles for preparing a film.

BACKGROUND ART

A polyion complex which is formed with an anionic polymer and a cationic polymer has already been known.

The use of a film made from a polyion complex for cosmetic purposes is also proposed by, for example, WO 2013/153678 and JP-A-2014-227389. The film disclosed in WO 2013/153678 and JP-A-2014-227389 can provide certain cosmetic effects.

However, the preparation of the film disclosed in WO 2013/153678 and JP-A-2014-227389 requires a spin coating process which needs a high speed rotation of a substrate, and therefore, it may be difficult to prepare the film in-situ on a keratin substrate such as skin.

JP-A-2015-107939 discloses the preparation of a film made from a polyion complex for cosmetic purposes by spraying a first solution of either of an anionic polymer and a cationic polymer, and spraying a second solution of the other of the anionic polymer and the cationic polymer, on a keratin substance, to mix the anionic and cationic polymers to form a film including the polyion complex. This preparation can prepare the film in-situ on a keratin substance such as skin.

However, it may be difficult to prepare the above film by the spraying process disclosed in JP-A-2015-107939 without careful control, because it may not be easy to control the amounts of the first and second solutions to be sprayed. In particular, the preparation of a relatively thick film by using the spraying process disclosed in JP-A-2015-107939 may be difficult.

One option to easily make a film made from a polyion complex may be to use a polyion complex in the form of particles. For example, JP-A-2005-36190 discloses a dispersion including polyion complex particles which has been formed by an anionic polymer and a cationic polymer.

DISCLOSURE OF INVENTION

However, it has been discovered that a dispersion including polyion complex particles is not always stable. If the dispersion is unstable, the polyion complex particles tend to precipitate.

Thus, a first objective of the present invention is to provide a stable composition such as a stable dispersion, which includes polyion complex particles.

The above objective of the present invention can be achieved by a composition, preferably a cosmetic composition, and more preferably a skin cosmetic composition comprising:
(a) at least one particle, comprising
  at least one cationic polymer,
  at least one anionic polymer, and
  at least one non-polymeric base having two or more pKb values or salt(s) thereof; and
(b) at least one physiologically acceptable volatile medium.

The cationic polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group.

The cationic polymer may be selected from the group consisting of cyclopolymers of alkyldiallylamine and cyclopolymers of dialkyldiallylammonium such as (co)polydiallyldialkyl ammonium chloride, (co)polyamines such as (co)polylysines and chitosan, cationic (co)polyaminoacids such as collagen, and salts thereof.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The anionic polymer may be selected from the group consisting of polysaccharides such as alginic acid, hyaluronic acid, and cellulose polymers, anionic (co)polyaminoacids such as (co)polyglutamic acids, (co)poly(meth)acrylic acids, (co)polyamic acids, (co)polystyrene sulfonate, (co)poly(vinyl sulfate), dextran sulfate, chondroitin sulfate, (co)polymaleic acids, (co)polyfumaric acids, maleic acid (co)polymers, and salts thereof.

The amount of either the cationic polymer or the anionic polymer, or both the cationic and anionic polymers, in the composition according to the present invention may be from 0.001 to 25% by weight, preferably from 0.1 to 20% by weight, and more preferably from 0.2 to 15% by weight, relative to the total weight of the composition.

The non-polymeric base having two or more pKb values may have at least two basic groups selected from the group consisting of an amino group, a guanidine group, a biguanide group, an imidazole group, an imino group, a pyridyl group and a mixture thereof.

The non-polymeric base having two or more pKb values or salt(s) thereof may be selected from the group consisting of arginine, lysine, histidine, cysteine, tyrosine, tryptophan, ornithine, and a mixture thereof.

The amount of the non-polymeric base having two or more pKb values or salt(s) thereof in the composition according to the present invention may be from 0.0001 to 30% by weight, preferably from 0.001 to 20% by weight, and more preferably from 0.002 to 15% by weight, relative to the total weight of the composition.

The (a) particle may comprises (c) at least one hydrophobic amino acid other than the non-polymeric base having two or more pKb values.

The amount of the (a) particle in the composition according to the present invention may be from 0.001 to 60% by weight, preferably from 0.1 to 50% by weight, and more preferably from 1 to 40% by weight, relative to the total weight of the composition.

The amount of the (b) at least one physiologically acceptable volatile medium, preferably water, in the composition may be from 50 to 99% by weight, preferably from 60 to 97% by weight, and more preferably from 70 to 95% by weight, relative to the total weight of the composition.

The pH of the composition according to the present invention may be from 3 to 9, preferably from 3.5 to 8.5, and more preferably from 4 to 8.

A second objective of the present invention is to provide a process which can easily prepare a film made from polyion complex particles.

The above objective of the present invention can be achieved by a process for preparing a film, preferably a cosmetic film, comprising:
applying onto a substrate, preferably a keratin substrate, and more preferably skin, the composition according to the present invention; and
drying the composition.

A third objective of the present invention is to provide a film made from polyion complex particles.

The above objective of the present invention can be achieved by:
(1) A film, preferably a cosmetic film, prepared by a process comprising:
applying onto a substrate, preferably a keratin substrate, and more preferably skin, the composition according to the present invention; and
drying the composition,
or
(2) A film, preferably a cosmetic film, comprising:
at least one cationic polymer,
at least one anionic polymer, and
at least one non-polymeric base having two or more pKb values or salt(s) thereof.

The present invention also relates to a cosmetic process for a keratin substrate such as skin, comprising
applying to the keratin substrate the composition according to the present invention; and
drying the composition to form a cosmetic film on the keratin substrate.

The cosmetic film thus obtained can be resistant to water with a pH of 7 or less, and can be removable with water with a pH of more than 7, preferably 8 or more, and more preferably 9 or more.

The present invention also relates to a use of the composition according to the present invention for the preparation of a cosmetic film on a keratin substrate such as skin, wherein the cosmetic film is resistant to water with a pH of 7 or less, and is removable with water with a pH of more than 7, preferably 8 or more, and more preferably 9 or more.

BEST MODE FOR CARRYING OUT THE INVENTION

After diligent research, the inventors have discovered that it is possible to provide a stable composition such as a stable dispersion, which includes polyion complex particles by combining the polyion complex particles with non-polymeric base(s) having two or more dissolution constants or salt(s) thereof. Thus, the composition according to the present invention comprises:
(a) at least one particle, comprising
at least one cationic polymer,
at least one anionic polymer, and
at least one non-polymeric base having two or more pKb values or salt(s) thereof; and
(b) at least one physiologically acceptable volatile medium.

Further, the inventors have discovered that it is possible to provide a process which can easily prepare a film comprising polyion complex particles. Thus, the process according to the present invention is a process for preparing a film, preferably a cosmetic film, the process comprising
applying onto a substrate, preferably a keratin substrate, the composition according to the present invention; and
drying the composition.

Furthermore, the inventors have discovered that it is possible to provide a film comprising polyion complex particles. Thus, the film according to the present invention is (1) A film, preferably a cosmetic film, prepared by a process comprising:
applying onto a substrate, preferably a keratin substrate, and more preferably skin, the composition according to the present invention; and
drying the composition,
or
(2) A film, preferably a cosmetic film, comprising:
at least one cationic polymer,
at least one anionic polymer, and
at least one non-polymeric base having two or more pKb values or salt(s).

The composition according to the present invention is stable for a long period of time, and can be used to easily prepare a film of a polyion complex by applying the composition onto a substrate, preferably a keratin substrate such as skin and hair, and more preferably skin, and drying the composition.

The polyion complex film according to the present invention can have a variety of cosmetic functions.

For example, the film according to the present invention itself may have cosmetic effects such as moisturizing due to the oil(s), as well as absorbing or adsorbing malodor, changing the appearance of a keratin substrate such as skin, changing the feel to the touch of the keratin substrate, and/or protecting the keratin substrate from, for example, dirt or pollutants.

If the polyion complex film includes at least one cosmetic active ingredient, the film can have cosmetic effects provided by the cosmetic active ingredient(s). For example, if the polyion complex film includes at least one cosmetic active ingredient selected from UV filters, anti-aging agents, anti-sebum agents, deodorant agents, anti-perspirant agents, whitening agents and a mixture thereof, the film can filter UV rays, treat the aging of the skin, absorb sebum on the skin, control odors on the skin, control the perspiration on the skin, and/or whiten the skin.

The film according to the present invention may be transparent, and therefore, may not be easy to perceive, even when the film is relatively thick.

Further, the film according to the present invention is water-resistant, and therefore, it can remain on a keratin substrate such as skin even if the surface of the keratin substrate is wet due to, for example sweat and rain.

Furthermore, the film according to the present invention can be easily removed from a keratin substrate such as skin under alkaline conditions. Therefore, the film according to the present invention is difficult to remove with water, while it can be easily removed with a soap which can provide alkaline conditions.

Thus, if the film according to the present invention includes a hydrophilic or water-soluble UV filter, the film according to the present invention can show UV shielding effects which are resistant to water (water-proof) and can be long-lasting, but can be easily removed with a soap which can provide alkaline conditions.

Hereinafter, the composition, process, film and the like according to the present invention will be explained in a more detailed manner.
[Polyion Complex Particle]

The composition according to the present invention includes (a) at least one particle which is a polyion complex particle. There is no limit to the type of the (a) particle. Two or more different types of (a) particles may be used in combination. Thus, a single type of (a) particle or a combination of different types of (a) particles may be used.

The size of the polyion complex particle may be from 1 nm to 10 μm, preferably from 5 nm to 5 μm, more preferably from 10 nm to 3 m. A particle size less than 1 μm can be measured by a dynamic light scattering method, and a particle size more than 1 μm can be measured by an optical microscope. This particle size may be based on number average diameter.

The amount of the (a) particle(s) in the composition according to the present invention may be 0.001% by weight or more, preferably 0.1% by weight or more, and more preferably 1% by weight or more, relative to the total weight of the composition.

The amount of the (a) particle(s) in the composition according to the present invention may be 60% by weight or less, preferably 50% by weight or less, and more preferably 40% by weight or less, relative to the total weight of the composition.

The amount of the (a) particle(s) in the composition according to the present invention may be from 0.001 to 60% by weight, preferably from 0.1 to 50% by weight, and more preferably from 1 to 40% by weight, relative to the total weight of the composition.

It is preferable that the (a) particle be amphiphilic and insoluble in oil or water.

The (a) particle includes at least one cationic polymer and at least one anionic polymer. There is no limit to the type of the cationic and anionic polymers. Two or more different types of cationic polymers may be used in combination. Thus, a single type of cationic polymer or a combination of different types of cationic polymers may be used. Two or more different types of anionic polymers may be used in combination. Thus, a single type of anionic polymer or a combination of different types of anionic polymers may be used.

The ratio of the amount, for example the chemical equivalent, of the cationic polymer(s)/the anionic polymer(s) may be 0.05-18, preferably 0.1-10, and more preferably 0.5-5.0. In particular, it may be preferable that the number of the cationic groups of the cationic polymer(s)/the number of anionic groups of the anionic polymer(s) be 0.05-18, more preferably 0.1-10, and even more preferably 0.5-5.0.

The total amount of the cationic and anionic polymers in the composition according to the present invention may be 0.001% by weight or more, preferably 0.1% by weight or more, and more preferably 0.3% by weight or more, relative to the total weight of the composition.

The total amount of the cationic and anionic polymers in the composition according to the present invention may be 25% by weight or less, preferably 20% by weight or less, and more preferably 15% by weight or less, relative to the total weight of the composition.

The total amount of the cationic and anionic polymers in the composition according to the present invention may be from 0.001 to 25% by weight, preferably from 0.1 to 20% by weight, and more preferably from 0.3 to 15% by weight, relative to the total weight of the composition.

(Cationic Polymer)

A cationic polymer has a positive charge density. The charge density of the cationic polymer may be from 0.01 meq/g to 20 meq/g, preferably from 0.05 to 15 meq/g, and more preferably from 0.1 to 10 meq/g.

It may be preferable that the molecular weight of the cationic polymer be 500 or more, preferably 1000 or more, more preferably 2000 or more, and even more preferably 5000 or more.

Unless otherwise defined in the descriptions, "molecular weight" means a number average molecular weight.

The cationic polymer may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group. The term (primary) "amino group" here means a group of —$NH_2$.

The cationic polymer may be a homopolymer or a copolymer. The term "copolymer" is understood to mean both copolymers obtained from two kinds of monomers and those obtained from more than two kinds of monomers, such as terpolymers obtained from three kinds of monomers.

The cationic polymer may be selected from natural and synthetic cationic polymers. Non-limiting examples of the cationic polymers are as follows.

(1) Homopolymers and copolymers derived from acrylic or methacrylic esters and amides and comprising at least one unit chosen from units of the following formulas:

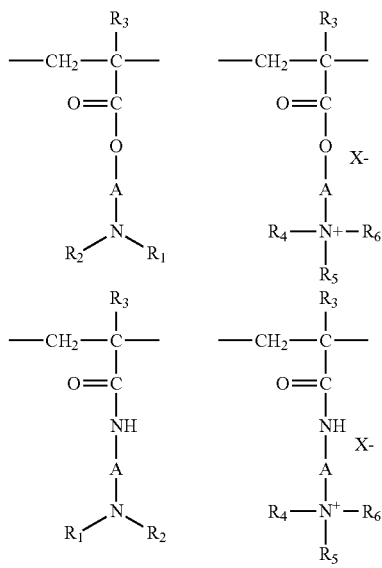

wherein:
$R_1$ and $R_2$, which may be identical or different, are chosen from hydrogen and alkyl groups comprising from 1 to 6 carbon atoms, for instance, methyl and ethyl groups;
$R_3$, which may be identical or different, is chosen from hydrogen and $CH_3$;
the symbols A, which may be identical or different, are chosen from linear or branched alkyl groups comprising from 1 to 6 carbon atoms, for example, from 2 to 3 carbon atoms and hydroxyalkyl groups comprising from 1 to 4 carbon atoms;
$R_4$, $R_5$, and $R_6$, which may be identical or different, are chosen from alkyl groups comprising from 1 to 18 carbon atoms and benzyl groups, and in at least one embodiment, alkyl groups comprising from 1 to 6 carbon atoms; and
X is an anion derived from an inorganic or organic acid, such as methosulphate anions and halides, for instance chloride and bromide.

The copolymers of family (1) may also comprise at least one unit derived from comonomers which may be chosen from acrylamides, methacrylamides, diacetone acrylamides, acrylamides and methacrylamides substituted on the nitrogen atom with ($C_1$-$C_4$) lower alkyl groups, groups derived from acrylic or methacrylic acids and esters thereof, vinyl-lactams such as vinylpyrrolidone and vinylcaprolactam, and vinyl esters.

Examples of copolymers of family (1) include, but are not limited to:

copolymers of acrylamide and of dimethylaminoethyl methacrylate quaternized with dimethyl sulphate or with a dimethyl halide, copolymers of acrylamide and of methacryloyloxyethyltrimethylammonium chloride described, for example, in European Patent Application No. 0 080 976, copolymers of acrylamide and of methacryloyloxyethyltrimethylammonium methosulphate, quaternized or nonquaternized vinylpyrrolidone/dialkylaminoalkyl acrylate or methacrylate copolymers, described, for example, in French Patent Nos. 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmethacrylamide copolymers, and crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing an olefinic unsaturation, for example, methylenebisacrylamide.

(2) Cationic cellulose derivatives such as cellulose ether derivatives comprising quaternary ammonium groups described, for example, in French Patent No. 1 492 597, such as the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers and cellulose derivatives grafted with a water-soluble monomer of quaternary ammonium, and described, for example, in U.S. Pat. No. 4,131,576, such as hydroxyalkylcelluloses, for instance, hydroxymethyl-, hydroxyethyl-, and hydroxypropylcelluloses grafted, for example, with a salt chosen from methacryloylethyltrimethylammonium, methacrylamidopropyltrimethylammonium, and dimethyldiallylammonium salts.

Commercial products corresponding to these polymers include, for example, the products sold under the name "Celquat® L 200" and "Celquat® H 100" by the company National Starch.

(4) Non-cellulose-based cationic polysaccharides described in U.S. Pat. Nos. 3,589,578 and 4,031,307, such as guar gums comprising cationic trialkylammonium groups, cationic hyaluronic acid, and dextran hydroxypropyl trimonium chloride. Guar gums modified with a salt, for example the chloride, of 2,3-epoxypropyltrimethylammonium (guar hydroxypropyltrimonium chloride) may also be used.

Such products are sold, for instance, under the trade names JAGUAR® C13 S, JAGUAR® C15, JAGUAR® C17, and JAGUAR® C162 by the company MEYHALL.

(5) Polymers comprising piperazinyl units and divalent alkylene or hydroxyalkylene groups comprising straight or branched chains, optionally interrupted with at least one entity chosen from oxygen, sulphur, nitrogen, aromatic rings, and heterocyclic rings, and also the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides possibly being cross-linked with an entity chosen from epihalohydrins; diepoxides; dianhydrides; unsaturated dianhydrides; bisunsaturated derivatives; bishalohydrins; bisazetidiniums; bishaloacyidiamines; bisalkyl halides; oligomers resulting from the reaction of a difunctional compound which is reactive with an entity chosen from bishalohydrins, bisazetidiniums, bishaloacyldiamines, bisalkyl halides, epihalohydrins, diepoxides, and bisunsaturated derivatives; the crosslinking agent being used in an amount ranging from 0.025 to 0.35 mol per amine group of the polyamino amide; these polyamino amides optionally being alkylated or, if they comprise at least one tertiary amine function, they may be quaternized. Such polymers are described, for example, in French Patent Nos. 2 252 840 and 2 368 508.

(7) Polyamino amide derivatives resulting from the condensation of polyalkylene polyamines with polycarboxylic acids, followed by alkylation with difunctional agents, for example, adipic acid/dialkylaminohydroxyalkyldialkylenetriamine polymers in which the alkyl group comprises from 1 to 4 carbon atoms, such as methyl, ethyl, and propyl groups, and the alkylene group comprises from 1 to 4 carbon atoms, such as an ethylene group. Such polymers are described, for instance, in French Patent No. 1 583 363. In at least one embodiment, these derivatives may be chosen from adipic acid/dimethylaminohydroxypropyldiethylenetriamine polymers.

(8) Polymers obtained by reaction of a polyalkylene polyamine comprising two primary amine groups and at least one secondary amine group, with a dicarboxylic acid chosen from diglycolic acid and saturated aliphatic dicarboxylic acids comprising from 3 to 8 carbon atoms. The molar ratio of the polyalkylene polyamine to the dicarboxylic acid may range from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

(9) Cyclopolymers of alkyldiallylamine and cyclopolymers of dialkyldiallyl-ammonium, such as homopolymers and copolymers comprising, as the main constituent of the chain, at least one unit chosen from units of formulas (Ia) and (Ib):

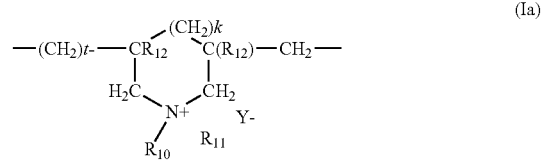

(Ia)

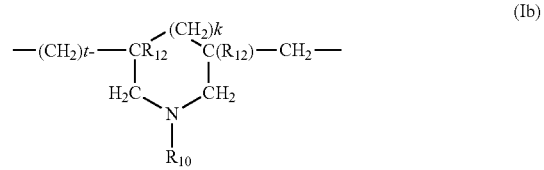

(Ib)

wherein:
k and t, which may be identical or different, are equal to 0 or 1, the sum k+t being equal to 1;
$R_{12}$ is chosen from hydrogen and methyl groups;
$R_{10}$ and $R_{11}$, which may be identical or different, are chosen from alkyl groups comprising from 1 to 6 carbon atoms, hydroxyalkyl groups in which the alkyl group comprises, for example, from 1 to 5 carbon atoms, and lower ($C_1$-$C_4$) amidoalkyl groups, or $R_{10}$ and $R_{11}$ may form, together with the nitrogen atom to which they are attached, heterocyclic groups such as piperidinyl and morpholinyl; and
Y' is an anion such as bromide, chloride, acetate, borate, citrate, tartrate, bisulphate, bisulphite, sulphate, and phosphate. These polymers are described, for example, in French Patent No. 2 080 759 and in its Certificate of Addition 2 190 406.

In one embodiment, $R_{10}$ and $R_{11}$, which may be identical or different, are chosen from alkyl groups comprising from 1 to 4 carbon atoms.

Examples of such polymers include, but are not limited to, (co)polydiallyldialkyl ammonium chloride such as the dimethyldiallylammonium chloride homopolymer sold under the name "MERQUAT® 100" by the company CALGON (and its homologues of low weight-average molecular mass) and the copolymers of diallyldimethylammonium chloride and of acrylamide sold under the name "MERQUAT® 550".

Quaternary diammonium polymers comprising at least one repeating unit of formula (II):

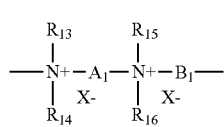

(II)

wherein:
$R_{13}$, $R_{14}$, $R_{15}$, and $R_{16}$, which may be identical or different, are chosen from aliphatic, alicyclic, and arylaliphatic groups comprising from 1 to 20 carbon atoms and lower hydroxyalkyl aliphatic groups, or alternatively $R_{13}$, $R_{14}$, $R_{15}$, and $R_{16}$ may form, together or separately, with the nitrogen atoms to which they are attached, heterocycles optionally comprising a second heteroatom other than nitrogen, or alternatively $R_{13}$, $R_{14}$, $R_{15}$, and $R_{16}$, which may be identical or different, are chosen from linear or branched $C_1$-$C_6$ alkyl groups substituted with at least one group chosen from nitrile groups, ester groups, acyl groups, amide groups, —CO—O—$R_{17}$-E groups, and —CO—NH—$R_{17}$-E groups, wherein $R_{17}$ is an alkylene group and E is a quaternary ammonium group;
$A_1$ and $B_1$, which may be identical or different, are chosen from polymethylene groups comprising from 2 to 20 carbon atoms, which may be linear or branched, saturated or unsaturated, and which may comprise, linked or intercalated in the main chain, at least one entity chosen from aromatic rings, oxygen, sulphur, sulphoxide groups, sulphone groups, disulphide groups, amino groups, alkylamino groups, hydroxyl groups, quaternary ammonium groups, ureido groups, amide groups, and ester groups, and
$X^-$ is an anion derived from an inorganic or organic acid;
$A_1$, $R_{13}$, and $R_{15}$ may form, together with the two nitrogen atoms to which they are attached, a piperazine ring;
if $A_1$ is chosen from linear or branched, saturated or unsaturated alkylene or hydroxyalkylene groups, $B_1$ may be chosen from:

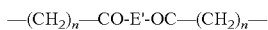

wherein E' is chosen from:
a) glycol residues of formula —O—Z—O—, wherein Z is chosen from linear or branched hydrocarbon-based groups and groups of the following formulas:

—($CH_2$—$CH_2$—O)$_x$—$CH_2$—$CH_2$—

—[$CH_2$—CH($CH_3$)—O]$_y$—$CH_2$—CH($CH_3$)— wherein x and y, which may be identical or different, are chosen from integers ranging from 1 to 4, which represent a defined and unique degree of polymerization, and numbers ranging from 1 to 4, which represent an average degree of polymerization;
b) bis-secondary diamine residue such as piperazine derivatives;
c) bis-primary diamine residues of formula —NH—Y—NH—, wherein Y is chosen from linear or branched hydrocarbon-based groups and the divalent group —$CH_2$—$CH_2$—S—S—$CH_2$—$CH_2$—; and
d) ureylene groups of formula —NH—CO—NH—.

In at least one embodiment, $X^-$ is an anion such as chloride or bromide.

Polymers of this type are described, for example, in French Patent Nos. 2 320 330; 2 270 846; 2 316 271; 2 336 434; and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

Non-limiting examples of such polymers include those comprising at least one repeating unit of formula (III):

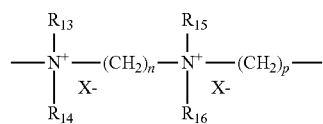

(III)

wherein $R_{13}$, $R_{14}$, $R_{15}$, and $R_{16}$, which may be identical or different, are chosen from alkyl and hydroxyalkyl groups comprising from 1 to 4 carbon atoms, n and p, which may be identical or different, are integers ranging from 2 to 20, and $X^-$ is an anion derived from an inorganic or organic acid.

(11) Polyquaternary ammonium polymers comprising units of formula (IV):

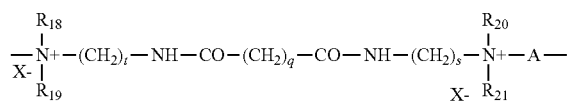

(IV)

wherein:
$R_{18}$, $R_{19}$, $R_{20}$, and $R_{21}$, which may be identical or different, are chosen from hydrogen, methyl groups, ethyl groups, propyl groups, O-hydroxyethyl groups, β-hydroxypropyl groups, —$CH_2CH_2$(O$CH_2CH_2$)$_p$OH groups, wherein p is chosen from integers ranging from 0 to 6, with the proviso that $R_{18}$, $R_{19}$, $R_{20}$, and $R_{21}$ are not simultaneously hydrogen, r and s, which may be identical or different, are chosen from integers ranging from 1 to 6,
q is chosen from integers ranging from 0 to 34,
$X^-$ is an anion such as a halide, and
A is chosen from radicals of dihalides and —$CH_2$—$CH_2$—O—$CH_2$—$CH_2$—.

Such compounds are described, for instance, in European Patent Application No. 0 122 324.

(12) Quaternary polymers of vinylpyrrolidone and of vinylimidazole.

Other examples of suitable cationic polymers include, but are not limited to, cationic proteins and cationic protein hydrolysates, polyalkyleneimines, such as polyethyleneimines, polymers comprising units chosen from vinylpyridine and vinylpyridinium units, condensates of polyamines and of epichlorohydrin, quaternary polyureylenes, and chitin derivatives.

According to one embodiment of the present invention, the at least one cationic polymer is chosen from cellulose ether derivatives comprising quaternary ammonium groups, such as the products sold under the name "JR 400" by the company UNION CARBIDE CORPORATION, cationic cyclopolymers, for instance, the homo-polymers and copolymers of dimethyldiallylammonium chloride sold under the names MERQUAT® 100, MERQUAT® 550, and MERQUAT® S by the company CALGON, guar gums modified with a 2,3-epoxypropyltrimethylammonium salt, and quaternary polymers of vinylpyrrolidone and of vinylimidazole.

(13) Polyamines

As the cationic polymer, it is also possible to use (co) polyamines, which may be homopolymers or copolymers, with a plurality of amino groups. The amino group may be a primary, secondary, tertiary or quaternary amino group. The amino group may be present in a polymer backbone or a pendent group, if present, of the (co)polyamines.

As example of the (co)polyamines, mention may be made of chitosan, (co)polyallylamines, (co)polyvinylamines, (co) polyanilines, (co)polyvinylimidazoles, (co)polydimethylaminoethylenemethacrylates, (co)polyvinylpyridines such as (co)poly-1-methyl-2-vinylpyridines, (co)polyimines such as (co) polyethyleneimines, (co)polypyridines such as (co) poly(quaternary pyridines), (co)polybiguanides such as (co) polyaminopropyl biguanides, (co)polylysines, (co)polyornithines, (co)polyarginines, (co)polyhistidines, aminodextrans, aminocelluloses, amino(co)polyvinylacetals, and salts thereof.

As the (co)polyamines, it is preferable to use (co)polylysines. Polylysine is well known. Polylysine can be a natural homopolymer of L-lysine that can be produced by bacterial fermentation. For example, polylysine can be e-Poly-L-lysine, typically used as a natural preservative in food products. Polylysine is a polyelectrolyte which is soluble in polar solvents such as water, propylene glycol and glycerol. Polylysine is commercially available in various forms, such as poly D-lysine and poly L-lysine. Polylysine can be in salt and/or solution form.

(14) Cationic Polyaminoacids

As the cationic polymer, it may be possible use cationic polyaminoacids, which may be cationic homopolymers or copolymers, with a plurality of amino groups and carboxyl groups.

The amino group may be a primary, secondary, tertiary or quaternary amino group. The amino group may be present in a polymer backbone or a pendent group, if present, of the cationic polyaminoacids. The carboxyl group may be present in a pendent group, if present, of the cationic polyaminoacids.

As examples of the cationic polyaminoacids, mention may be made of cationized collagen, cationized gelatin, steardimoium hydroxyprolyl hydrolyzed wheat protein, cocodimonium hydroxypropyl hydrolyzed wheat protein, hydroxypropyltrimonium hydrolyzed conchiolin protein, steardimonium hydroxypropyl hydrolyzed soy protein, hydroxypropyltrimonium hydrolyzed soy protein, cocodimonium hydroxypropyl hydrolyzed soy protein, and the like.

It may be preferable that the cationic polymer be selected from the group consisting of cyclopolymers of alkyldiallylamine and cyclopolymers of dialkyldiallylammonium such as (co)polydiallyldialkyl ammonium chloride, (co) polyamines such as (co)polylysines and chitosan, cationic (co)polyaminoacids such as cationized collagen, and salts thereof.

The amount of the cationic polymer(s) in the composition according to the present invention may be 0.001% by weight or more, preferably 0.1% by weight or more, and more preferably 1% by weight or more, relative to the total weight of the composition.

The amount of the cationic polymer(s) in the composition according to the present invention may be 25% by weight or less, preferably 20% by weight or less, and more preferably 15% by weight or less, relative to the total weight of the composition.

The amount of the cationic polymer(s) in the composition according to the present invention may be from 0.001 to 25% by weight, preferably from 0.1 to 20% by weight, and more preferably from 1 to 15% by weight, relative to the total weight of the composition.

(Anionic Polymer)

An anionic polymer has a positive charge density. The charge density of the anionic polymer may be from 0.1 meq/g to 20 meq/g, preferably from 1 to 15 meq/g, and more preferably from 4 to 10 meq/g if the anionic polymer is a synthetic anionic polymer, and the average substitution degree of the anionic polymer may be from 0.1 to 3.0, preferably from 0.2 to 2.7, and more preferably from 0.3 to 2.5 if the anionic polymer is a natural anionic polymer.

It may be preferable that the molecular weight of the anionic polymer be 1,000 or more, preferably 10,000 or more, more preferably 50,000 or more, and even more preferably 1,000,00 or more.

The anionic polymer may have at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

The anionic polymer may be a homopolymer or a copolymer. The term "copolymer" is understood to mean both copolymers obtained from two kinds of monomers and those obtained from more than two kinds of monomers, such as terpolymers obtained from three kinds of monomers.

The anionic polymer may be selected from natural and synthetic anionic polymers.

The anionic polymer may comprise at least one hydrophobic chain.

The anionic polymer which may comprise at least one hydrophobic chain may be obtained by copolymerization of a monomer (a) chosen from carboxylic acids comprising α,β-ethylenic unsaturation (monomer a') and 2-acrylamido-2-methylpropanesulphonic acid (monomer a") with a non-surface-active monomer (b) comprising an ethylenic unsaturation other than (a) and/or a monomer (c) comprising an ethylenic unsaturation resulting from the reaction of an acrylic monomer comprising an α,β-monoethylenic unsaturation or of an isocyanate monomer comprising a monoethylenic unsaturation with a monohydric nonionic amphiphilic component or with a primary or secondary fatty amine.

Thus, the anionic polymer with at least one hydrophobic chain may be obtained by two synthetic routes:

either by copolymerization of the monomers (a') and (c), or (a'), (b) and (c), or (a") and (c), or (a"), (b) and (c), or by modification (and in particular esterification or amidation) of a copolymer formed from the monomers (a') or from the monomers (a') and (b), or (a") and (b), by a monohydric nonionic amphiphilic compound or a primary or secondary fatty amine.

Mention may in particular be made, as 2-acrylamido-2-methylpropanesulphonic acid copolymers, of those disclosed in the article "Micelle formation of random copolymers of sodium 2-(acrylamido)-2-methylpropanesulfonate and nonionic surfactant macromonomer in water as studied by fluorescence and dynamic light scattering—Macromolecules, 2000, Vol. 33, No. 10-3694-3704" and in applications EP-A-0 750 899 and EP-A-1 069 172.

The carboxylic acid comprising an α,β-monoethylenic unsaturation constituting the monomer (a') can be chosen from numerous acids and in particular from acrylic acid, methacrylic acid, crotonic acid, itaconic acid and maleic acid. It is preferably acrylic or methacrylic acid.

The copolymer can comprise a monomer (b) comprising a monoethylenic unsaturation which does not have a surfactant property. The preferred monomers are those which give water-insoluble polymers when they are homopolymerized. They can be chosen, for example, from $C_1$-$C_4$ alkyl acrylates and methacrylates, such as methyl acrylate, ethyl acrylate, butyl acrylate or the corresponding methacrylates. The more particularly preferred monomers are methyl acrylate and ethyl acrylate. The other monomers which can be used are, for example, styrene, vinyltoluene, vinyl acetate, acrylonitrile and vinylidene chloride. Unreactive monomers are preferred, these monomers being those in which the single ethylenic group is the only group which is reactive under the polymerization conditions. However, monomers which comprise groups which react under the effect of heat, such as hydroxyethyl acrylate, can optionally be used.

The monomer (c) is obtained by reaction of an acrylic monomer comprising α,β-monoethylenic unsaturation, such as (a), or of an isocyanate monomer comprising monoethylenic unsaturation with a monohydric nonionic amphiphilic compound or a primary or secondary fatty amine.

The monohydric nonionic amphiphilic compounds or the primary or secondary fatty amines used to produce the nonionic monomer (c) are well known. The monohydric nonionic amphiphilic compounds are generally alkoxylated hydrophobic compounds comprising an alkylene oxide forming the hydrophilic part of the molecule. The hydrophobic compounds are generally composed of an aliphatic alcohol or an alkylphenol, in which compounds a carbonaceous chain comprising at least six carbon atoms constitutes the hydrophobic part of the amphiphilic compound.

The preferred monohydric nonionic amphiphilic compounds are compounds having the following formula (V):

$$R-(OCH_2CHR')_m-(OCH_2CH_2)_n-OH \quad (V)$$

in which R is chosen from alkyl or alkylene groups comprising from 6 to 30 carbon atoms and alkylaryl groups having alkyl radicals comprising from 8 to 30 carbon atoms, R' is chosen from alkyl groups comprising from 1 to 4 carbon atoms, n is a mean number ranging from approximately 1 to 150 and m is a mean number ranging from approximately 0 to 50, provided that n is at least as great as m.

Preferably, in the compounds of formula (V), the R group is chosen from alkyl groups comprising from 12 to 26 carbon atoms and alkylphenyl groups in which the alkyl group is $C_8$-$C_{13}$; the R' group is the methyl group; m=0 and n=1 to 25.

The preferred primary and secondary fatty amines are composed of one or two alkyl chains comprising from 6 to 30 carbon atoms.

The monomer used to form the nonionic urethane monomer (c) can be chosen from highly varied compounds. Use may be made of any compound comprising a copolymerizable unsaturation, such as an acrylic, methacrylic or allylic unsaturation. The monomer (c) can be obtained in particular from an isocyanate comprising a monoethylenic unsaturation, such as, in particular, α,α-dimethyl-m-isopropenylbenzyl isocyanate.

The monomer (c) can be chosen in particular from acrylates, methacrylates or itaconates of oxyethylenated (1 to 50 EO) $C_6$-$C_{30}$ fatty alcohol, such as steareth-20 methacrylate, oxyethylenated (25 EO) behenyl methacrylate, oxyethylenated (20 EO) monocetyl itaconate, oxyethylenated (20 EO) monostearyl itaconate or the acrylate modified by polyoxyethylenated (25 EO) $C_{12}$-$C_{24}$ alcohols and from dimethyl-m-isopropenylbenzyl isocyanates of oxyethylenated (1 to 50 EO) $C_6$-$C_{30}$ fatty alcohol, such as, in particular, the dimethyl-m-isopropenylbenzyl isocyanate of oxyethylenated behenyl alcohol.

According to a specific embodiment of the present invention, the anionic polymer is chosen from acrylic terpolymers obtained from (a) a carboxylic acid comprising an α,β-ethylenic unsaturation, (b) a non-surface-active monomer comprising an ethylenic unsaturation other than (a), and (c) a nonionic urethane monomer which is the reaction product of a monohydric nonionic amphiphilic compound with an isocyanate comprising a monoethylenic unsaturation.

Mention may in particular be made, as anionic polymers comprising at least one hydrophobic chain, of the acrylic acid/ethyl acrylate/alkyl acrylate terpolymer, such as the product as a 30% aqueous dispersion sold under the name Acusol 823 by Rohm & Haas; the acrylates/steareth-20 methacrylate copolymer, such as the product sold under the name Aculyn 22 by Rohm & Haas; the (meth)acrylic acid/ethyl acrylate/oxyethylenated (25 EO) behenyl methacrylate terpolymer, such as the product as an aqueous emulsion sold under the name Aculyn 28 by Rohm & Haas; the acrylic acid/oxyethylenated (20 EO) monocetyl itaconate copolymer, such as the product as a 30% aqueous dispersion sold under the name Structure 3001 by National Starch; the acrylic acid/oxyethylenated (20 EO) monostearyl itaconate copolymer, such as the product as a 30% aqueous dispersion sold under the name Structure 2001 by National Starch; the acrylates/acrylate modified by polyoxyethylenated (25 EO) $C_{12}$-$C_{24}$ alcohol copolymer, such as the 30-32% copolymer latex sold under the name Synthalen W2000 by 3V SA; or the methacrylic acid/methyl acrylate/dimethyl-meta-isopropenylbenzyl isocyanate of ethoxylated behenyl alcohol terpolymer, such as the product as a 24% aqueous dispersion and comprising 40 ethylene oxide groups disclosed in the document EP-A-0 173 109.

The anionic polymers may also be Polyester-5, such as the product sold under the name of Eastman AQ™ 55S Polymer by EASTMAN CHEMICAL having a chemical formula below.

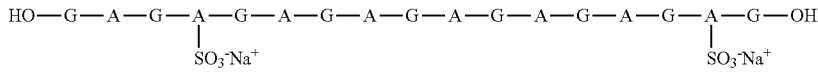

A: dicarboxylic acid moiety
G: glycol moiety
SO$_3^-$Na$^+$: sodium sulfo group
OH: hydroxyl group It may be preferable that the anionic polymer be selected from the group consisting of polysaccharides such as alginic acid, hyaluronic acid, and cellulose polymers (e.g., carboxymethylcellulose), anionic (co)polyaminoacids such as (co)polyglutamic acids, (co)poly(meth)acrylic acids, (co)polyamic acids, (co)polystyrene sulfonate, (co)poly(vinyl sulfate), dextran sulfate, chondroitin sulfate, (co)polymaleic acids, (co)polyfumaric acids, maleic acid (co)polymers, and salts thereof.

The maleic acid copolymer may comprise one or more maleic acid comonomers, and one or more comonomers chosen from vinyl acetate, vinyl alcohol, vinylpyrrolidone, olefins comprising from 2 to 20 carbon atoms, and styrene.

Thus, the "maleic acid copolymer" is understood to mean any polymer obtained by copolymerization of one or more maleic acid comonomers and of one or more comonomers chosen from vinyl acetate, vinyl alcohol, vinylpyrrolidone, olefins comprising from 2 to 20 carbon atoms, such as octadecene, ethylene, isobutylene, diisobutylene or isooctylene, and styrene, the maleic acid comonomers optionally being partially or completely hydrolysed. Use will preferably be made of hydrophilic polymers, that is to say polymers having a solubility of water of greater than or equal to 2 g/l.

In an advantageous aspect of the present invention, the maleic acid copolymer may have a molar fraction of maleic acid units of between 0.1 and 1, more preferably between 0.4 and 0.9.

The weight-average molar mass of the maleic acid copolymer may be between 1,000 and 500,000, and preferably between 1,000 and 50,000.

It is preferable that the maleic acid copolymer be a styrene/maleic acid copolymer, and more preferably sodium styrene/maleic acid copolymer.

Use will preferably be made of a copolymer of styrene and of maleic acid in a 50/50 ratio.

Use may be made, for example, of the styrene/maleic acid (50/50) copolymer, in the form of an ammonium salt at 30% in water, sold under the reference SMA1000H® by Cray Valley or the styrene/maleic acid (50/50) copolymer, in the form of a sodium salt at 40% in water, sold under the reference SMA1000HNa® by Cray Valley.

The use of the styrene/maleic acid copolymer such as sodium styrene/maleic acid copolymer can improve the wettability of a film prepared by the composition according to the present invention.

The amount of the anionic polymer(s) in the composition according to the present invention may be 0.001% by weight or more, preferably 0.1% by weight or more, and more preferably 1% by weight or more, relative to the total weight of the composition.

The amount of the anionic polymer(s) in the composition according to the present invention may be 25% by weight or less, preferably 20% by weight or less, and more preferably 15% by weight or less, relative to the total weight of the composition.

The amount of the anionic polymer(s) in the composition according to the present invention may be from 0.001 to 25% by weight, preferably from 0.1 to 20% by weight, and more preferably from 1 to 15% by weight, relative to the total weight of the composition.

(Non-Polymeric Base Having Two or More Base Dissociation Constants)

The composition according to the present invention may include at least one non-polymeric base having two or more pKb values or salt(s) thereof, i.e., at least one non-polymeric base having two or more base dissociation constants or salt(s) thereof. The pKb value (base dissociation constant) is well known to those skilled in the art, and should be determined at a constant temperature such as 25° C.

The non-polymeric base having two or more pKb values or salt(s) thereof can be included in the (a) particle. The non-polymeric base having two or more pKb values can function as a crosslinker for the cationic and anionic polymers.

The term "non-polymeric" here means that the base is not obtained by polymerizing two or more monomers. Therefore, the non-polymeric base does not correspond to a base obtained by polymerizing two or more monomers such as polyallylamine.

It is preferable that the molecular weight of the non-polymeric base having two or more pKb values or salt(s) thereof be 1000 or less, preferably 800 or less, and more preferably 700 or less.

There is no limit to the type of the non-polymeric base having two or more pKb values or salt(s) thereof. Two or more different types of non-polymeric bases having two or more pKb values or salts thereof may be used in combination. Thus, a single type of a non-polymeric base having two or more pKb values or a salt thereof or a combination of different types of non-polymeric bases having two or more pKb values or salts thereof may be used.

The term "salt" in the present specification means a salt formed by addition of suitable acid(s) to the non-polymeric base having two or more pKb values, which may be obtained from a reaction with the non-polymeric base having two or more pKb values with the acid(s) according to methods known to those skilled in the art. As the salt, mention may be made of ammonium salts, for example salts with inorganic acid such as HCl and HNO$_3$, and salts with organic acid such as carboxylic acids and sulfonic acids.

The non-polymeric base having two or more pKb values or salt(s) thereof may be an organic base or salt(s) thereof, and preferably a hydrophilic or water-soluble organic base or salt(s) thereof.

The non-polymeric base having two or more pKb values may have at least two basic groups selected from the group consisting of an amino group, a guanidine group, a biguanide group, an imidazole group, an imino group, a pyridyl group and a mixture thereof.

The non-polymeric base having two or more pKb values may be selected from the group consisting of non-polymeric diamines such as ethylenediamine, propylenediamine, pentanediamine, hexanediamine, urea and derivatives thereof and guanidine and derivatives thereof, non-polymeric polyamines such as spermine and spermidine, basic amino acids, and a mixture thereof.

The non-polymeric base having two or more pKb values or salt(s) thereof may be selected from the group consisting of arginine, lysine, histidine, cysteine, cystine, tyrosine, tryptophan, ornithine, and a mixture thereof.

It may be preferable that the non-polymeric base having two or more pKb values or salt(s) thereof be selected from the group consisting of arginine, lysine, histidine, and a mixture thereof.

The amount of the non-polymeric base having two or more pKb values or salt(s) thereof in the composition according to the present invention may be 0.0001% by weight or more, preferably 0.001% by weight or more, and more preferably 0.002% by weight or more, relative to the total weight of the composition.

The amount of the non-polymeric base having two or more pKb values or salt(s) thereof in the composition according to the present invention may be 30% by weight or less, preferably 20% by weight or less, and more preferably 15% by weight or less, relative to the total weight of the composition.

The amount of the non-polymeric base having two or more pKb values or salt(s) thereof in the composition according to the present invention may be from 0.0001 to 30% by weight, preferably from 0.001 to 20% by weight, and more preferably from 0.002 to 15% by weight, relative to the total weight of the composition.

[Hydrophobic Amino Acid]

The (a) particle in the composition according to the present invention may include (c) at least one hydrophobic amino acid other than the above non-polymeric base having two or more pKb values or salt(s) thereof. Two or more hydrophobic amino acids may be used in combination.

The term "hydrophobic amino acid" may be selected from the group consisting of isoleucine, leucine, valine, methionine, phenylalanine, threonine, glycine, cysteine, alanine and mixtures thereof. It is preferable that the (c) hydrophobic amino acid be selected from leucine, phenylalanine and mixtures thereof.

The (c) hydrophobic amino acid may be useful for controlling the hydrophobicity of the (a) particle.

The amount of the (c) hydrophobic amino acid(s) in the composition according to the present invention may be 0.001% by weight or more, preferably 0.01% by weight or more, and more preferably 0.1% by weight or more, relative to the total weight of the composition.

The amount of the (c) hydrophobic amino acid(s) in the composition according to the present invention may be 10% by weight or less, preferably 5% by weight or less, and more preferably 1% by weight or less, relative to the total weight of the composition.

The amount of the (c) hydrophobic amino acid(s) in the composition according to the present invention may be from 0.001 to 10% by weight, preferably from 0.01 to 5% by weight, and more preferably from 0.1 to 1% by weight, relative to the total weight of the composition.

[Physiologically Acceptable Volatile Medium]

The composition according to the present invention comprises at least one (b) physiologically acceptable volatile medium.

The term "physiologically acceptable" volatile medium is intended to denote a volatile medium that is particularly suitable for applying the composition according to the present invention to keratin substance(s).

The term "volatile" means that the (b) physiologically acceptable medium can evaporate under a normal atmospheric pressure such as 1 atm and at room temperature such as 25° C.

The physiologically acceptable medium is generally adapted to the nature of the support onto which the composition according to the present invention is to be applied, and also to the form in which the composition according to the present invention is to be packaged.

The (b) physiologically acceptable volatile medium may comprise at least one hydrophilic organic solvent, water or a mixture thereof.

As the hydrophilic organic solvent, mention may be made of, for example, monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 8 carbon atoms, such as glycerol, propylene glycol, butylene glycol, pentylene glycol, hexylene glycol, caprylyl glycol, dipropylene glycol or diethylene glycol; glycol ethers (especially containing from 3 to 16 carbon atoms) such as mono-, di- or tripropylene glycol ($C_1$-$C_4$) alkyl ethers, mono-, di- or triethylene glycol ($C_1$-$C_4$)alkyl ethers, and mixtures thereof.

The amount of the (b) at least one physiologically acceptable volatile medium, preferably water, in the composition according to the present invention may be from 50 to 99% by weight, preferably from 60 to 97% by weight, and more preferably from 70 to 95% by weight, relative to the total weight of the composition.

[Cosmetic Active Ingredient]

The composition according to the present invention may comprise at least one cosmetic active ingredient. There is no limitation to the cosmetic active ingredient. Two or more cosmetic active ingredients may be used in combination. Thus, a single type of cosmetic active ingredient or a combination of different types of cosmetic active ingredients may be used.

Among the cosmetic active ingredients to be used, mention may be made of UV filters, anti-oxidants, cleansing agents, free radical scavengers, moisturizers, whitening agents, liporegulators, anti-acne agents, antidandruff agents, anti-aging agents, softeners, anti-wrinkle agents, keratolitic agents, fresheners, antibacterial agents, antifungal agents, antiperspirants, deodorants, skin conditioners, anesthetics, nourishing agents, and sebum absorbers or moisture absorbers.

It is preferable that the non-polymeric base having two or more pKb values can function as a cosmetic active agent. If the non-polymeric base having two or more pKb values can function as a cosmetic active agent, it may not be necessary for the composition according to the present invention to include cosmetic active agent(s).

The composition according to the present invention may comprise the cosmetic active ingredient(s) in an amount of from 0.01 to 50% by weight, preferably from 0.1 to 40% by weight, more preferably from 1 to 30% by weight, and even more preferably 2 to 20% by weight, relative to the total weight of the composition.

(UV Filter)

According to a preferred embodiment of the present invention, the cosmetic active ingredient may be selected from UV filters.

There is no limit to the type of UV filter. Two or more types of UV filters may be used in combination. Thus, a single type of UV filter or a combination of different types of UV filters may be used. The UV filter can be selected from the group consisting of an inorganic UV filter, an organic UV filter, and a mixture thereof.

(Inorganic UV Filter)

The composition according to the present invention may comprise at least one inorganic UV filter. If two or more inorganic UV filters are used, they may be the same or different, preferably the same.

The inorganic UV filter used for the present invention may be active in the UV-A and/or UV-B region. The inorganic UV filter may be hydrophilic and/or lipophilic. The inorganic UV filter is preferably insoluble in solvents such as water and ethanol commonly used in cosmetics.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Preferably, the inorganic UV filters may be selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilanes, polydimethylsiloxanes, and polymethylhydrosiloxanes.

Of course, the inorganic UV filters made of metal oxides may, before their treatment with silicones, have been treated with other surfacing agents, in particular, with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated with:

silica, such as the product "Sunveil" from Ikeda;

silica and iron oxide, such as the product "Sunveil F" from Ikeda;

silica and alumina, such as the products "Microtitanium Dioxide MT 500 SA" from Tayca, "Tioveil" from Tioxide, and "Mirasun TiW 60" from Rhodia;

alumina, such as the products "Tipaque TTO-55 (B)" and "Tipaque TTO-55 (A)" from Ishihara, and "UVT 14/4" from Kemira;

alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;

alumina and aluminum laurate, such as the product "Microtitanium Dioxide MT 100 S" from Tayca;

iron oxide and iron stearate, such as the product "Microtitanium Dioxide MT 100 F" from Tayca;

zinc oxide and zinc stearate, such as the product "BR351" from Tayca;

silica and alumina and treated with a silicone, such as the products "Microtitanium Dioxide MT 600 SAS", "Microtitanium Dioxide MT 500 SAS", and "Microtitanium Dioxide MT 100 SAS" from Tayca;

silica, alumina, and aluminum stearate and treated with a silicone, such as the product "STT-30-DS" from Titan Kogyo;

silica and treated with a silicone, such as the product "UV-Titan X 195" from Kemira; alumina and treated with a silicone, such as the products "Tipaque TTO-55 (S)" from Ishihara or "UV Titan M 262" from Kemira;

triethanolamine, such as the product "STT-65-S" from Titan Kogyo;

stearic acid, such as the product "Tipaque TTO-55 (C)" from Ishihara; or sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm;

Dimethicone (and) Stearic Acid (and) Aluminum Hydroxide (and) $TiO_2$, such as the product "SA-TTO-S4" from Miyoshi Kasei, with a mean primary particle diameter of 15 nm; Silica (and) $TiO_2$, such as the product "MT-100 WP" from Tayca, with a mean primary particle diameter of 15 nm;

Dimethicone (and) Silica (and) Aluminum Hydroxide (and) $TiO_2$, such as the product "MT-Y02" and "MT-Y-110 M3S" from Tayca, with a mean primary particle diameter of 10 nm;

Dimethicone (and) Aluminum Hydroxide (and) $TiO_2$, such as the product "SA-TTO-S3" from Miyoshi Kasei, with a mean primary particle diameter of 15 nm;

Dimethicone (and) Alumina (and) $TiO_2$, such as the product "UV TITAN M170" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS", and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and
those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane);
those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture);
those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica, and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

If the inorganic UV filter(s) in the form of fine particles is/are used, a film according to the present invention which can be prepared from the composition according to the present invention may also have an effect of not providing a white appearance but a transparent or clear appearance, because the fine particles of the inorganic UV filters do not aggregate but can be spread uniformly or homogeneously in the film. It should be noted that free fine particles of inorganic UV filter(s) easily aggregate to give a white appearance to the skin.

(Organic UV Filter)

The composition according to the present invention may comprise at least one organic UV filter. If two or more organic UV filters are used, they may be the same or different, preferably the same.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadiene compounds; guaiazulene and derivatives thereof; rutin and derivatives thereof; and mixtures thereof.

Mention may be made, as examples of the organic UV filter(s), of those denoted below under their INCI names, and mixtures thereof.

Anthranilic compounds: Menthyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark <<TINOSORB S>> by CIBA GEIGY, and ethylhexyl triazone marketed under the trademark <<UVINUL T150>> by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071, 5,166,355, GB-2,303,549, DE-197,26,184 and EP-893, 119, and Drometrizole trisiloxane, marketed under the trademark "Silatrizole" by Rhodia Chimie or "Mexoryl XL" by L'Oreal, as represented below.

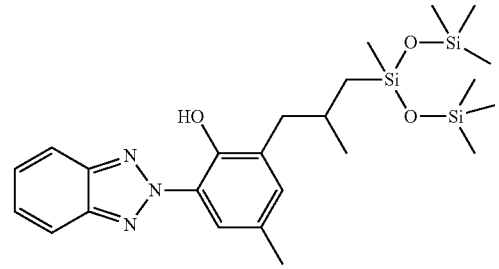 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1 (dimethylpropyl) benzoxazol-2-yl-(4-phenyl)imino]-6-(2-ethylhexyl) imino-1,3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,1'-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl) imino-1,3,5-triazine, camphor benzylkonium methosulfate and mixtures thereof.

It is possible that the UV filter be water-soluble or water-dispersible, in particular, water-soluble. As an example of the water-soluble UV filter, mention may be made of Mexoryl SX. Normally, the water-soluble or water-dispersible UV filter can be removed from the surface of a keratinous substrate such as skin by water such as sweat and rain. However, since the water-soluble or water-dispersible UV filter is included in the film according to the present invention which can be prepared from the composition according to the present invention, it is difficult for the water-soluble or water-dispersible UV filter to be removed from film by water, thereby resulting in long-lasting UV shielding effects.

(Whitening Agent)

According to a preferred embodiment of the present invention, the cosmetic active ingredient may be selected from whitening agents.

There is no limit to the type of whitening agent. Two or more types of whitening agents may be used in combination. Thus, a single type of whitening agent or a combination of different types of whitening agents may be used.

As examples of the whitening agent, mention may be made of ascorbic acid or derivatives thereof, kojic acid or derivatives thereof, tranexamic acid or derivatives thereof, resorcinol or derivatives thereof, alkoxysalicylic acid or salts thereof, adenosine phosphate or salts thereof, hydroquinone or glycosides thereof or derivatives thereof, glutathione, 4-(4-hydroxyphenyl)-2-butanol, magnolignan (5,5'-dipropyl-biphenyl-2,2'-diol), *Chamomilla recutita*, and the like.

Ascorbic acid has a D-configuration or L-configuration, and the L-configuration one is preferably employed. Ascorbic acid is also referred to as vitamin C, and has effects of inhibiting the production of melanin due to the strong reduction effects of ascorbic acid. The derivatives of ascorbic acid may be salts of ascorbic acid, and the salts of ascorbic acid are preferably selected from sodium ascorbate, magnesium ascorbyl phosphate, and sodium ascorbyl phosphate. The derivatives of ascorbic acids may be glycosides of ascorbic acid or esters of ascorbic acid. As an example of glycosides of ascorbic acid, mention may be made of, for example, ascorbyl glucoside. As examples of esters of ascorbic acid, mention may be made of, for example, silyl ascorbate, tocopheryl ascorbate, and alkyl ascorbate. As the alkyl ascorbate, methyl ascorbate or ethyl ascorbate is preferably used. In particular, ascorbyl glucoside is preferable. Ascorbic acid or derivatives thereof can be used alone or in combination with two or more types thereof.

As detailed examples of derivatives of ascorbic acid, mention may be made of, for example, 5,6-di-O-dimethylsilyl ascorbate, which is commercially available as PRO-AA from Exsymol SAM; dl-alpha-tocopheryl-2-1-ascorbyl phosphate which is commercially available as SEPIVITAL EPC from Senju Pharmaceutical Co., Ltd.; sodium ascorbyl phosphate which is commercially available as Stay-C 50 from Roche; ascorbyl glucoside which is commercially available from Hayashibara Biochemical Labs., Inc.; 3-O-ethyl ascorbic acid; and the like.

Ascorbic acid or the derivative thereof is preferably used in combination with a copolymer of styrene and maleic anhydride. In particular, at least one part of the maleic anhydride unit of the aforementioned copolymer is preferably hydrolyzed. The aforementioned hydrolyzed maleic anhydride unit may be in the form of an alkaline salt such as a sodium salt, a potassium salt, a lithium salt, or the like. The aforementioned maleic anhydride unit preferably occupies 0.4 to 0.9 mol per one mol of the entire copolymer, and a ratio of the maleic anhydride unit and the styrene unit is preferably 50:50. In particular, it is preferable that the ratio of the maleic anhydride unit and the styrene unit be preferably 50:50, and the ammonium salt or sodium salt be used. By employing ascorbic acid or the derivative thereof in combination with the aforementioned copolymer, stability of ascorbic acid or the derivative thereof is improved. As the aforementioned copolymer, for example, a copolymer of styrene and maleic anhydride (50/50) in the form of an ammonium salt in a concentration of 30% in water, which is commercially available as product number SMA 1000 H (trademark) from Atofina Chemicals Inc.; or a copolymer of styrene and maleic anhydride (50/50) in the form of a sodium salt in a concentration of 40% in water, which is commercially available as product number SMA 1000 H Na (trademark) from Atofina Chemicals Inc., can be used. The aforementioned copolymer is used in a concentration ranging from 0.1 to 20% by weight, and preferably ranging from 0.1 to 10% by weight, with respect to the total weight of the whitening agent for topical application.

As an example of derivatives of kojic acid, mention may be made of, for example, kojic acid glucoside.

As examples of derivatives of tranexamic acid, mention may be made of dimers of tranexamic acid (such as hydrochloric acid trans-4-(trans-aminomethylcyclohexanecarbonyl)aminomethylcyclohexane carboxylic acid), esters of tranexamic acid and hydroquinone (such as 4'-hydroxyphenyl trans-4-aminomethylcyclohexane carboxylate), esters of tranexamic acid and gentisic acid (such as 2-(trans-4-aminomethylcyclohexanecarbonyloxy)-5-hydroxybenzoic acid and salts thereof), tranexamic amides (such as trans-4-aminomethylcyclohexanecarboxylic acid methylamide and salts thereof, trans-4-(p-methoxybenzoyl)aminomethylcyclohexane carboxylic acid and salts thereof, and trans-4-guanidinomethylcyclohexane carboxylic acid and salts thereof), and the like.

As examples of derivatives of resorcinol, mention may be made of, for example, 4-n-butylresorcinol (Rucinol) and the like.

An alkoxysalicylic acid is a compound in which any one of hydrogen atoms in the 3-position, the 4-position, or the 5-position of salicylic acid is substituted by an alkoxy group. The aforementioned alkoxy group is preferably any one of a methoxy group, an ethoxy group, a propoxy group, an isopropoxy group, a butoxy group, and isobutoxy group, and is more preferably a methoxy group or an ethoxy group. As examples of the compound, mention may be made of, for example, 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, 5-propoxysalicylic acid, and the like. Salts of the alkoxysalicylic acids are not particularly limited. As examples thereof, mention may be made of, for example, alkali metal salts or alkaline earth metal salts such as sodium salts, potassium salts, calcium salts, and the like, ammonium salts, amino acid salts, and the like. A potassium salt of 4-methoxysalicylic acid is preferable.

As examples of adenosine phosphate or salts thereof, mention may be made of, for example, disodium adenosine phosphate, and the like.

As examples of glycosides of hydroquinone, mention may be made of, for example, hexose glycosides such as hydroquinone alpha-D-glucose, hydroquinone beta-D-glucose, hydroquinone alpha-L-glucose, hydroquinone beta-L-glucose, hydroquinone alpha-D-galactose, hydroquinone beta-D-galactose, hydroquinone alpha-L-galactose, hydroquinone beta-L-galactose, and the like; pentose glycosides such as hydroquinone alpha-D-ribose, hydroquinone beta-D-ribose, hydroquinone alpha-L-ribose, hydroquinone beta-L-ribose, hydroquinone alpha-D-arabinose, hydroquinone beta-D-arabinose, hydroquinone alpha-L-arabinose, hydroquinone beta-L-arabinose, and the like; aminosugar glycosides such as hydroquinone alpha-D-glucosamine, hydroquinone beta-D-glucosamine, hydroquinone alpha-L-glucosamine, hydroquinone beta-L-glucosamine, hydroquinone alpha-D-galactosamine, hydroquinone beta-D-galactosamine, hydroquinone alpha-L-galactosamine, hydroquinone beta-L-galactosamine, and the like; urocanic acid glycosides such as hydroquinone alpha-D-glucuronic acid, hydroquinone beta-D-glucuronic acid, hydroquinone alpha-L-glucuronic acid, hydroquinone beta-L-glucuronic acid, hydroquinone alpha-D-galacturonic acid, hydroquinone beta-D-galacturonic acid, hydroquinone alpha-L-galacturonic acid, hydroquinone beta-L-galacturonic acid, and the like; and the like. Among these compounds, hydroquinone beta-D-glucose (hereinafter, referred to as "arbutin") is preferable. As examples of derivatives of hydroquinone or glycosides thereof, mention may be made of, for example, salts of hydroquinone or glycosides thereof. In particular, as examples of arbutin derivatives, mention may be made of, for example, 6-O-caffeoylarbutin, and the like.

As the whitening active ingredients, in particular, L-ascorbic acid or derivatives thereof, kojic acid or derivatives thereof, tranexamic acid or derivatives thereof, arbutin or derivatives thereof, and Rucinol are preferable, and ascorbic acid derivatives such as 3-O-ethyl L-ascorbic acid and L-ascorbic acid glucoside are more preferable.

[pH]

The pH of the composition according to the present invention may be from 3 to 9, preferably from 3.5 to 8.5, and more preferably from 4 to 8.

At a pH of from 3 to 9, the (a) particle can be very stable.

The pH of the composition according to the present invention may be adjusted by adding at least one alkaline agent other than the non-polymeric base having two or more pKb values and/or at least one acid, as explained below. The pH of the composition according to the present invention may also be adjusted by adding at least one buffering agent.

(Alkaline Agent)

The composition according to the present invention may comprise at least one alkaline agent. Two or more alkaline agents may be used in combination. Thus, a single type of alkaline agent or a combination of different types of alkaline agents may be used.

It is preferable that the alkaline agent have only one pKb.

The alkaline agent may be an inorganic alkaline agent. It is preferable that the inorganic alkaline agent be selected from the group consisting of ammonia; alkaline metal hydroxides; alkaline earth metal hydroxides; and a mixture thereof.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As an inorganic alkaline agent, sodium hydroxide is preferable.

The alkaline agent may be an organic alkaline agent. It is preferable that the organic alkaline agent be selected from the group consisting of monoamines and derivatives thereof.

The alkaline agent(s) may be used in a total amount of from 0.1 to 20% by weight, preferably from 0.2 to 10% by weight, more preferably from 0.3 to 5% by weight, relative to the total weight of the composition, depending on their solubility.

(Acid)

The composition according to the present invention may comprise at least one acid. Two or more acids may be used in combination. Thus, a single type of acid or a combination of different types of acids may be used.

It is preferable that the acid have only one pKa.

As the acid, mention may be made of any inorganic or organic acids, preferably inorganic acids, which are commonly used in cosmetic products. A monovalent acid may be used. A monovalent acid such as citric acid, lactic acid, sulfuric acid, phosphoric acid and hydrochloric acid (HCl) may be used. HCl is preferable.

The acid(s) may be used in a total amount of from 0.1 to 15% by weight, preferably from 0.2 to 10% by weight, more preferably from 0.3 to 5% by weight, relative to the total weight of the composition, depending on their solubility.

(Buffering Agent)

The composition according to the present invention may comprise at least one buffering agent. Two or more buffering agents may be used in combination. Thus, a single type of buffering agent or a combination of different types of buffering agents may be used.

As the buffering agent, mention may be made of an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), Hepes buffer (4-(2-hydroxyethyl)-1-piperazineethanesulfonic acid).

[Optional Additives]

The composition according to the present invention may comprise, in addition to the aforementioned components, components typically employed in cosmetics, specifically, such as dyes, powders, surfactants or emulsifiers, oils, thickeners, organic non-volatile solvents, silicones and silicone derivatives, natural extracts derived from animals or vegetables, waxes, and the like, within a range which does not impair the effects of the present invention.

The composition according to the present invention may comprise the above optional additive(s) in an amount of from 0.01 to 50% by weight, preferably from 0.05 to 30% by weight, and more preferably from 0.1 to 10% by weight, relative to the total weight of the composition.

In one embodiment, the composition according to the present invention may include at least one oil. Two or more oils may be used in combination. Thus, a single type of oil or a combination of different types of oils may be used. Herein, the term "oil" is understood to mean a fatty substance which is liquid at ambient temperature (25° C.).

The oil(s) may be volatile or non-volatile.

The oil(s) may be of animal, plant, mineral or synthetic origin.

The term "non-volatile oil" means an oil that remains on a keratin substance at room temperature (25° C.) and atmospheric pressure. More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

The term "volatile oil" means any non-aqueous medium that is capable of evaporating on contact with the skin or the lips in less than one hour, at room temperature (25° C.) and atmospheric pressure. The volatile oil is a cosmetic volatile oil, which is liquid at room temperature (25° C.). More specifically, a volatile oil has an evaporation rate of between 0.01 and 200 mg/cm$^2$/min, limits included.

(Volatile Oils)

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity of less than or equal to 8 centistokes (cSt) (8×10$^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the present invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to one embodiment, the cosmetic composition according to the present invention may comprise from 1 to 80% by weight, or even from 5 to 70% by weight, or even from 10 to 60% by weight and especially from 15 to 50% by weight of volatile oil relative to the total weight of the composition.

(Non-Volatile Oils)

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin, such as perhydrosqualene, hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, winter squash oil, millet oil, barley oil, quinoa oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, musk rose oil, sesame oil, soybean oil, sunflower oil, castor oil and watermelon seed oil, and mixtures thereof, or alternatively caprylic/capric acid triglycerides, such as those sold by the company Stearineries Dubois or those sold under the names Miglyol 810®, 812® and 818® by the company Dynamit Nobel, linear or branched hydrocarbons of mineral or synthetic origin, such as liquid paraffins and derivatives thereof, petroleum jelly, polydecenes, polybutenes, hydrogenated polyisobutene such as Parleam, and squalane;

synthetic ethers containing from 10 to 40 carbon atoms;

synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that the sum of the number of carbon atoms in the chains $R_1$ and $R_2$ is greater than or equal to 10. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate, polyol esters and pentaerythritol esters, for instance dipentaerythrityl tetrahydroxystearate/tetraisostearate, esters of diol dimers and of diacid dimers, such as Lusplan DD-DA5® and Lusplan DD-DA7® sold by the company Nippon Fine Chemical and described in patent application US 2004-175 338, copolymers of polyols and of diacid dimers, and esters thereof, such as Hailuscent ISDA or the dilinoleic acid/butanediol copolymer, fatty alcohols that are liquid at room temperature (25° C.), with a branched and/or unsaturated carbon-based chain containing from 12 to 26 carbon atoms, for instance 2-octyldodecanol, stearyl alcohol, isostearyl alcohol, cetyl alcohol, oleyl alcohol, 2-hexyldecanol, 2-butyloctanol and 2-undecylpentadecanol;

$C_{12}$-$C_{22}$ higher fatty acids, such as oleic acid, linoleic acid or linolenic acid, and mixtures thereof, dialkyl carbonates, the two alkyl chains possibly being identical or different, such as dicaprylyl carbonate sold under the name Cetiol CC® by Cognis, oils of high molar mass, in particular having a molar mass ranging from about 400 to about 10 000 g/mol, in particular from about 650 to about 10 000 g/mol, in particular from about 750 to about 7500 g/mol and more particularly ranging from about 1000 to about 5000 g/mol. As oils of high molar mass that may be used in the present invention, mention may especially be made of oils chosen from:

lipophilic polymers, linear fatty acid esters with a total carbon number ranging from 35 to 70, hydroxylated esters, aromatic esters, $C_{24}$-$C_{28}$ branched fatty acid or fatty alcohol esters, silicone oils, oils of plant origin, and mixtures thereof;

optionally partially hydrocarbon-based and/or silicone fluoro oils, for instance fluorosilicone oils, fluoropolyethers and fluorosilicones as described in document EP-A-847 752;

silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

(Emulsifier)

In another embodiment, the composition according to the present invention may include at least one emulsifier. Two or more emulsifiers may be used in combination. Thus, a single type of emulsifier or a combination of different types of emulsifiers may be used.

The emulsifier may be selected from nonionic, anionic, amphoteric, zwitterionic, cationic emulsifiers and mixtures thereof. Examples of emulsifiers include also natural or synthetic polymeric emulsifiers.

Anionic emulsifiers include alkyl and alkyl ether sulfates, alkyl sulfonates, alkyl and alkyl ether phosphates, alkyl or alkyl ether sulfosuccinates, alkyl and alkyl ether carboxylates, where the alkyl radical comprises from 8 to 30 carbon atoms and preferably from 10 to 22 carbon atoms, as well as anionic derivatives of alkyl polyglycosides, such as the citric, tartaric or sulfosuccinic ester of alkyl polyglucosides.

Nonionic emulsifiers can be broadly defined as compounds containing a hydrophobic moiety and a nonionic hydrophilic moiety. Examples of the hydrophobic moiety can be alkyl, alkyl aromatic, and aryl aromatic moieties. Examples of hydrophilic moieties are polyoxyalkylenes, amine oxides, and alkanol amides. Examples of non-ionic emulsifiers are alkoxylated fatty alcohols or fatty acids, alkoxylated di- and tri-styryl phenols, polyhydroxy fatty acid amides, sugar esters and polyesters, alkoxylated sugar esters, sorbitan and alkoxylated sorbitan fatty acid esters. Other examples of nonionic emulsifiers include alkyl polyglycosides, such as coco polyglucosides.

Cationic emulsifiers useful in the present invention may contain amino or quaternary ammonium hydrophilic moieties which are positively charged when dissolved in water.

Examples of ammonium compounds are long-chain alkyl trimethyl ammonium chloride, long-chain alkyl benzyl dimethyl ammonium chloride, alkylamine hydrochlorides, alkylamine acetates and di(long-chain alkyl) dimethyl ammonium bromide.

The amphoteric emulsifiers which can be used in the present invention may be those which can be broadly described as derivatives of aliphatic quaternary ammonium compounds, wherein one of the aliphatic substituents contains an anionic water-solubilizing group, e.g., carboxylate, sulfonate, sulfate. Examples of amphoteric surfactants include cocoamphocarboxypropionate, cocoamphoacetate, cocoamphodiacetate, sodium lauroamphoacetate.

Examples of zwitterionic emulsifiers include alkyl betaines and amido betaines, alkyl sultaines, alkyl glycinates and alkyl carboxyglycinates.

Polymeric emulsifiers include, but are not limited to, carboxylic acid polymers which are crosslinked compounds containing one or more monomers derived from acrylic acid, substituted acrylic acids, and salts and derivatives of these acrylic acids and substituted acrylic acids. These carboxylic acid polymers also act as thickening agents. They can be crosslinked homopolymers of an acrylic acid or of a derivative thereof, such as acrylamidopropylsulfonic acid. They can be also crosslinked copolymers having (i) a first monomer selected from the group consisting of (meth)acrylic acid, derivatives thereof, short chain (i.e. $C_1$-$C_4$) acrylate ester monomers, and mixtures thereof; and (ii) a second monomer which is a long chain (i.e. $C_8$-$C_{40}$) substituted polyethylene glycol acrylate ester monomer.

Examples of commercially available carboxylic acid polymers useful herein are Carbopol 1342, Pemulen TR-1 or TR-2 (INCI: Acrylates/C10-30 Alkyl Acrylate Crosspolymer, from Lubrizol Corp.); Sepigel 305, Simulgel EG, Simulgel NS, Simulgel 600 (from Seppic S.A.); Viscolam AT100P and Viscofam AT64/P (from Lamberti S.p.A.).

Other materials that may be suitable as polymeric emulsifiers include ethylene oxide/propylene oxide block copolymers, for example those commercialized under the trade name Pluronic (BASF).

Other suitable polymeric emulsifiers include natural polymer derivatives such as polysaccharides that may be derivatized with hydrophobic moieties. Further examples of suitable emulsifiers that can be used in the composition of the present invention are disclosed in "McCutcheon's Detergents and Emulsifiers", North American Edition (2003), Allured Publishing Corporation.

It is preferable that the emulsifier be selected from polymeric emulsifiers, more preferably from associative polymers, and even more preferably from Acrylates/C10-30 Alkyl Acrylate Crosspolymers such as Pemulen TR2.

The amount of the emulsifier(s) in the composition according to the present invention may be from 0.01 to 15% by weight, preferably from 0.05 to 10% by weight, and more preferably from 0.1 to 5% by weight, relative to the total weight of the composition.

[Composition]

The composition according to the present invention may be intended to be used as a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

Thus, the cosmetic composition according to the present invention may be a skin cosmetic composition, preferably a skin care composition or a skin makeup composition, in particular a composition for protecting skin from UV and/or pollutants in the air.

The composition according to the present invention may be in any form such as a solution, a dispersion, an emulsion, a gel, and a paste. If the composition according to the present invention includes (c) at least one oil, the composition according to the present invention may be in the form of an emulsion such as W/O, O/W, W/O/W and O/W/O, preferably a, O/W emulsion.

The composition according to the present invention can be prepared by mixing the above essential and optional ingredients in accordance with any of the processes which are well known to those skilled in the art.

[Film]

The composition according to the present invention can be used for easily preparing a film which may be relatively thick. The (a) particles can aggregate and integrate into a continuous film.

Thus, the present invention also relates to a process for preparing a film, preferably a cosmetic film, with a thickness of, preferably more than 0.1 µm, more preferably 0.5 µm or more, and even more preferably 1 µm or more, comprising: applying onto a substrate, preferably a keratin substrate, more preferably skin, the composition according to the present invention; and drying the composition.

The upper limit of the thickness of the film according to the present invention is not limited. Thus, for example, the thickness of the film according to the present invention may be 1 mm or less, preferably 500 µm or less, more preferably 300 µm or less, and even more preferably 100 µm or less.

Since the process for preparing a film according to the present invention includes the steps of applying the composition according to the present invention onto a substrate, preferably a keratin substrate, and more preferably skin, and of drying the composition, the process according to the present invention does not need any spin coating or spraying, and therefore, it is possible to easily prepare even a relatively thick film. Thus, the process for preparing a film according to present invention can prepare a relatively thick film without any special equipment such as spin coaters and spraying machines.

Even if the film according to the present invention is relatively thick, it is still thin and may be transparent, and therefore, may not be easy to perceive. Thus, the film according to the present invention can be used preferably as a cosmetic film.

If the substrate is not a keratin substrate such as skin, the composition according to the present invention may be applied onto a substrate made from any material other than keratin. The materials of the non-keratinous substrate are not limited. Two or more materials may be used in combination. Thus, a single type of material or a combination of different types of materials may be used. In any event, it is preferable that the substrate be flexible or elastic.

If the substrate is not a keratin substrate, it is preferable that the substrate be water-soluble, because it is possible to leave the film according to the present invention by washing the substrate with water. As examples of the water-soluble materials, mention may be made of poly(meth) acrylic acids, polyethyleneglycols, polyacrylamides, polyvinylalcohol (PVA), starch, celluloseacetates, and the like. PVA is preferable.

If the non-keratinous substrate is in the form of a sheet, it may have a thickness of more than that of the film according to the present invention, in order to ease the handling of the film attached to the substrate sheet. The thickness of the non-keratinous substrate sheet is not limited, but may be from 1 µm to 5 mm, preferably from 10 µm to 1 mm, and more preferably from 50 to 500 µm.

It is more preferable that the film according to the present invention be releasable from the non-keratinous substrate. The mode of release is not limited. Therefore, the film according to the present invention may be peeled from the non-keratinous substrate, or released by the dissolution of the substrate sheet into a solvent such as water.

The present invention also relates to:

(1) A film, preferably a cosmetic film, with a thickness of, preferably more than 0.1 µm, more preferably 0.5 µm or more, and even more preferably 1 µm or more, prepared by a process comprising:
applying onto a substrate, preferably a keratin substrate, and more preferably skin, the composition according to the present invention; and
drying the composition,
and (2) A film, preferably a cosmetic film, with a thickness of, preferably more than 0.1 µm, more preferably 0.5 µm or more, and even more preferably 1 µm or more, comprising:
at least one cationic polymer,
at least one anionic polymer, and
at least one non-polymeric base having two or more pKb values or salt(s) thereof.

The above explanations regarding the cationic and anionic polymers as well as the above non-polymeric base having two or more pKb values or salt(s) thereof can apply to those in the above film (1) and (2).

The film thus obtained above can be self-standing. The term "self-standing" here means that the film can be in the form of a sheet and can be handled as an independent sheet without the assistance of a substrate or support. Thus, the term "self-standing" may have the same meaning as "self-supporting".

It is preferable that the film according to the present invention be hydrophobic.

The term "hydrophobic" in the present specification means that the solubility of the polymer in water (preferably with a volume of 1 liter) at from 20 to 40° C., preferably from 25 to 40° C., and more preferably from 30 to 40° C. is less than 10% by weight, preferably less than 5% by weight, more preferably less than 1% by weight, and even more preferably less than 0.1% by weight, relative to the total weight of the polymer. It is most preferable that the polymer is not soluble in water.

If the film according to the present invention is hydrophobic, the film can have water-resistant properties, and therefore, it can remain on a keratin substrate such as skin even if the surface of the keratin substrate is wet due to, for example sweat and rain. Thus, when the film according to the present invention provides any cosmetic effect, the cosmetic effect can last a long time.

On the other hand, the film according to the present invention can be easily removed from a keratin substrate such as skin under alkaline conditions such as a pH of from 8 to 12, preferably from 9 to 11. Therefore, the film according to the present invention is difficult to remove with water, while it can be easily removed with a soap which can provide such alkaline conditions.

The film according to the present invention may comprise at least one biocompatible and/or biodegradable polymer layer. Two or more biocompatible and/or biodegradable polymers may be used in combination. Thus, a single type of biocompatible and/or biodegradable polymer or a combination of different types of biocompatible and/or biodegradable polymers may be used.

The term "biocompatible" polymer in the present specification means that the polymer does not have excess interaction between the polymer and cells in the living body including the skin, and the polymer is not recognized by the living body as a foreign material.

The term "biodegradable" polymer in the present specification means that the polymer can be degraded or decomposed in a living body due to, for example, the metabolism of the living body itself or the metabolism of the microorganisms which may be present in the living body. Also, the biodegradable polymer can be degraded by hydrolysis.

If the film according to the present invention includes a biocompatible and/or biodegradable polymer, it is less irritable or not irritable to the skin, and does not cause any rash. In addition, due to the use of a biocompatible and/or biodegradable polymer, the cosmetic sheet according to the present invention can adhere well to the skin.

The film according to the present invention can be used for cosmetic treatments of keratin substances, preferably skin, in particular the face. The film according to the present invention can be in any shape or form. For example, it can be used as a full-face mask sheet, or a patch for a part of the face such as the cheek, nose, and around the eyes.

If the film according to the present invention includes at least one hydrophilic or water-soluble UV filter, it can provide UV shielding effects derived from the hydrophilic or water-soluble UV filter. Normally, a hydrophilic or water-soluble UV filter can be removed from the surface of a keratinous substrate such as skin by water such as sweat and rain. However, since the hydrophilic or water-soluble UV filter is included in the film according to the present invention, it is difficult for the hydrophilic or water-soluble UV filter to be removed by water, thereby resulting in long-lasting UV shielding effects.

[Cosmetic Process and Use]

The present invention also relates to:
a cosmetic process for a keratin substrate such as skin, comprising: applying to the keratin substrate the composition the present invention; and drying the composition to form a cosmetic film on the keratin substrate; and
a use of the composition according to the present invention for the preparation of a cosmetic film on a keratin substrate such as skin.

The cosmetic process here means a non-therapeutic cosmetic method for caring for and/or making up the surface of a keratin substrate such as skin.

In both the above process and use, the above cosmetic film is resistant to water with a pH of 7 or less, and is removable with water with a pH of more than 7, preferably 8 or more, and more preferably 9 or more.

In other words, the above cosmetic film can be water-resistant under neutral or acidic conditions such as a pH of 7 or less, preferably in a range of 6 or more and 7 or less, and more preferably in a range of 5 or more and 7 or less, while the above cosmetic film can be removed under alkaline conditions such as a pH of more than 7, preferably 8 or more, and more preferably 9 or more. The upper limit of the pH is preferably 13, more preferably 12, and even more preferably 11.

Accordingly, the above cosmetic film can be water-resistant, and therefore, it can remain on a keratin substrate such as skin even if the surface of the keratin substrate is wet due to, for example sweat and rain. On the other hand, the above cosmetic film can be easily removed from a keratin substrate such as skin under alkaline conditions. Therefore, the film according to the present invention is difficult to remove with water, while it can be easily removed with a soap which can provide alkaline conditions.

If the above cosmetic film includes a UV filter which may be present in the composition according to the present invention, the above cosmetic film can protect a keratin substrate such as skin from UV rays, thereby limiting the darkening of the skin, improving the colour and uniformity of the complexion, and/or treating aging of the skin.

Furthermore, the above cosmetic film may have cosmetic effects such as absorbing or adsorbing malodor, changing the appearance of a keratin substrate such as skin, changing the feel to the touch of the keratin substrate, and/or protecting the keratin substrate from, for example, dirt or pollutant, due to the properties of the polyion complex particles in the cosmetic film, even if the cosmetic film does not include any cosmetic active ingredient.

In addition, the above cosmetic film may immediately change or modify the appearance of the skin by changing light reflection on the skin and the like, even if the cosmetic film does not include any cosmetic active ingredient. Therefore, it may be possible for the above cosmetic film to conceal skin defects such as pores or wrinkles. Further, the above cosmetic film may immediately change or modify the feel to the touch of the skin by changing the surface roughness on the skin and the like. Furthermore, the above cosmetic film may immediately protect the skin by covering the surface of the skin and shielding the skin, as a barrier, from environmental stresses such as pollutants, contaminants and the like.

The above cosmetic effects can be adjusted or controlled by changing the chemical composition, the thickness and/or the surface roughness of the above cosmetic film.

If the above cosmetic film includes at least one cosmetic active ingredient, the cosmetic film can have cosmetic effects provided by the cosmetic active ingredient(s). For example, if the cosmetic film includes at least one cosmetic active ingredient selected from anti-aging agents, anti-sebum agents, deodorant agents, anti-perspirant agents, whitening agents and a mixture thereof, the cosmetic film can treat the aging of the skin, absorbing sebum on the skin, controlling odors on the skin, controlling perspiration on the skin, and/or whitening of the skin.

It is also possible to apply a makeup cosmetic composition onto the cosmetic sheet according to the present invention after being applied onto the skin.

EXAMPLES

The present invention will be described in a more detailed manner by way of examples. However, they should not be construed as limiting the scope of the present invention.

[Preparation of Polyion Complex Particle]

Example 1

0.02 g of carboxymethylcellulose and 0.2 g of vegetable chitosan were dissolved into 60 g of water, and pH was adjusted to 2.5 by 4 wt % HCl aqueous solution. 1.5 g of an aqueous solution (10 wt %) of arginine was added to this mixture until pH reached 6.4. During the pH increase of the mixture, cationic polyion complex particles (cationic PGP), which were composed of carboxymethylcellulose (polyanion), chitosan (polycation) and arginine (cationic crosslinker), were successfully prepared.

The diameter of the cationic PGP was about 15 nm, and the potential of the cationic PGP was 30 mV.

The cationic PGP dispersion according to Example 1 was stable for 2 weeks at room temperature. Thus, no precipitates were visually observed for 2 weeks.

Example 2

0.05 g of carboxymethylcellulose and 0.2 g of vegetable chitosan were dissolved into 60 g of water, and pH was adjusted to 1.8 by 4 wt % HCl aqueous solution. 3 g of an aqueous solution (10 wt %) of arginine was added to this mixture until pH reached 4.9. During the pH increase of the mixture, particles of cationic PGP, which were composed of carboxymethylcellulose (polyanion), chitosan (polycation) and arginine (cationic crosslinker), were successfully prepared.

The diameter of the cationic PGP was about 370 nm, and the potential of the cationic PGP was 6 mV.

The cationic PGP dispersion according to Example 1 was stable for 2 weeks at room temperature. Thus, no precipitates were visually observed for 2 weeks.

(Evaluation)

50 mg of the cationic PGP dispersion according to each of Examples 1-2 was applied onto a surface of a polymethylmethacrylate (PMMA) plate (HELIOPLATE HD6) and dried at room temperature for 1 hour.

After drying, the PMMA plate was dipped into a calcium chloride solution (0.14 g/l) at room temperature for 15 minutes.

After dipping, the PMMA plate was pulled up, and dried for 1 hour. The surface of the PMMA plate was visually observed, and confirmed that a film was present on the PMMA plate for both Examples 1 and 2. The thickness of the obtained film was 0.6 µm.

The invention claimed is:

1. A composition, comprising:
   (a) at least one polyion complex particle formed of:
      at least one cationic polymer,
      at least one anionic polymer, and
      at least one non-polymeric base having two or more pKb values or salt thereof;
      wherein the at least one non-polymeric base having two or more pKb values crosslinks the at least one cationic polymer and the at least one anionic polymer to form the polyion complex particle, and wherein the at least one non-polymeric base having two or more pKb values is selected from the group consisting of arginine, lysine, histidine, ornithine, and a mixture thereof; and
   (b) at least one physiologically acceptable volatile medium.

2. The composition according to claim 1, wherein the at least one cationic polymer has at least one positively chargeable and/or positively charged moiety selected from the group consisting of a primary, secondary or tertiary amino group, a quaternary ammonium group, a guanidine group, a biguanide group, an imidazole group, an imino group, and a pyridyl group.

3. The composition according to claim 1, wherein the at least one cationic polymer is selected from the group consisting of cyclopolymers of alkyldiallylamine and cyclopolymers of dialkyldiallylammonium, cationic (co)polyaminoacids, and salts thereof.

4. The composition according to claim 1, wherein the at least one anionic polymer has at least one negatively chargeable and/or negatively charged moiety selected from the group consisting of a sulfuric group, a sulfate group, a sulfonic group, a sulfonate group, a phosphoric group, a phosphate group, a phosphonic group, a phosphonate group, a carboxylic group, and a carboxylate group.

5. The composition according to claim 1, wherein the at least one anionic polymer is selected from the group consisting of polysaccharides, anionic (co)polyaminoacids, (co)poly(meth)acrylic acids, (co)polyamic acids, (co)polystyrene sulfonate, (co)poly(vinyl sulfates), dextran sulfate, chondroitin sulfate, (co)polymaleic acids, polyfumaric acids, maleic acid (co)polymers, and salts thereof.

6. The composition according to claim 1, wherein the amount of either the at least one cationic polymer or the at least one anionic polymer, or both the at least one cationic and at least one anionic polymers, in the composition is from 0.001 to 25% by weight relative to the total weight of the composition.

7. The composition according to claim 1, wherein the amount of the at least one non-polymeric base having two or more pKb values or salt thereof in the composition is from 0.0001 to 30% by weight relative to the total weight of the composition.

8. The composition according to claim 1, wherein the (a) at least one polyion complex particle further comprises (c) at least one hydrophobic amino acid other than the non-polymeric base having two or more pKb values or salt thereof.

9. The composition according to claim 1, wherein the amount of the (a) at least one polyion complex particle in the composition is from 0.001 to 60% by weight relative to the total weight of the composition.

10. The composition according to claim 1, wherein the amount of the (b) at least one physiologically acceptable volatile medium in the composition is from 50 to 99% by weight relative to the total weight of the composition.

11. The composition according to claim 1, wherein the pH of the composition is from 3 to 9.

12. A process for preparing a film comprising:
    applying onto a substrate the composition according to claim 1; and
    drying the composition.

13. A film prepared by a process comprising:
    applying onto a substrate the composition according to claim 1; and
    drying the composition.

14. A cosmetic process for a keratin substrate, comprising
applying to the keratin substrate the composition according to claim 1; and
drying the composition to form a cosmetic film on the keratin substrate.

* * * * *